United States Patent

Morrill et al.

[11] Patent Number: 5,135,487
[45] Date of Patent: Aug. 4, 1992

[54] BALLOON DILATATION CATHETER WITH INTEGRAL GUIDEWIRE

[75] Inventors: Richard J. Morrill, Billerica; C. Vaughan Seifert, Boxboro; Lori K. Segar, Cambridge, all of Mass.

[73] Assignee: C. R. Bard, Inc., Murray Hill, N.J.

[21] Appl. No.: 696,334

[22] Filed: May 1, 1991

Related U.S. Application Data

[63] Continuation of Ser. No. 269,795, Nov. 10, 1988, abandoned.

[51] Int. Cl.$^5$ .................................................. A61M 29/00
[52] U.S. Cl. ..................................... 604/96; 606/194
[58] Field of Search .............................. 604/95-101, 604/282, 164; 606/192-194; 128/656, 657, 658, 772

[56] References Cited

U.S. PATENT DOCUMENTS

| | | | |
|---|---|---|---|
| 4,024,873 | 5/1977 | Antoshkiw et al. | 128/349 B |
| 4,195,637 | 4/1980 | Gruntzig et al. | 128/348 |
| 4,315,512 | 2/1982 | Fogarty | 128/344 |
| 4,323,071 | 4/1982 | Simpson et al. | 128/343 |
| 4,413,989 | 11/1983 | Schjeldahl et al. | 604/96 |
| 4,483,340 | 11/1984 | Fogarty et al. | 128/344 |
| 4,582,181 | 4/1986 | Samson | 606/194 |
| 4,616,653 | 10/1986 | Samson et al. | 604/95 |
| 4,638,805 | 1/1987 | Powell | 604/97 |
| 4,641,654 | 2/1987 | Samson et al. | 604/100 |
| 4,646,742 | 3/1987 | Packard et al. | 128/344 |
| 4,715,378 | 12/1987 | Pope, Jr. et al. | 604/96 |
| 4,723,936 | 2/1988 | Buchbinder et al. | 604/95 |
| 4,771,778 | 9/1988 | Mar | 606/192 |
| 4,793,350 | 12/1988 | Mar et al. | 604/96 |
| 4,838,268 | 6/1989 | Keith et al. | 604/96 |
| 4,848,344 | 7/1989 | Sos et al. | 604/194 |
| 4,906,241 | 3/1990 | Noddin et al. | 606/194 |

Primary Examiner—C. Fred Rosenbaum
Assistant Examiner—William W. Levis
Attorney, Agent, or Firm—Wolf, Greenfield & Sacks

[57] ABSTRACT

A balloon dilation catheter adapted for use in percutaneous transluminal coronary angioplasty has an integral guidewire. The balloon and its supporting members are not attached to the guidewire at their distal ends. The supporting members are attached at their proximal ends to the guidewire. The guidewire has an increased freedom of rotational movement and the balloon and its supporting members do not adversely twist about the guidewire.

71 Claims, 3 Drawing Sheets

BALLOON DILATATION CATHETER WITH INTEGRAL GUIDEWIRE

This application is a continuation of application Ser. No. 07/269,795, filed Nov. 10, 1988, now abandoned.

FIELD OF THE INVENTION

The invention relates to balloon dilation catheters and, particularly, catheters used for angioplasty.

BACKGROUND OF THE INVENTION

The invention concerns balloon dilatation catheters and, particularly, to balloon dilatation catheters of the type used in percutaneous transluminal coronary angioplasty (PTCA) in which a stenosed region of a coronary artery is dilated to increase the blood flow through that artery. The PTCA procedure typically involves advancement of a guide catheter from a percutaneous puncture in the femoral or brachial artery to place the distal end of the guide catheter at the entrance to the coronary arteries. With the guide catheter positioned, a balloon dilatation catheter is passed through the guide catheter into the coronary arteries. The balloon dilatation catheter typically is used in conjunction with a small diameter steerable guidewire which can be manipulated into the selected arterial branch to be treated. After the guidewire has been manipulated into place, the balloon catheter is advanced, with the balloon in a deflated state, over the guidewire into the stenosis. The balloon then is inflated to dilate the artery.

Early PTCA catheters used a separate guidewire. The development of improved techniques by physicians, however, lead to attempts to enter and dilate very narrow stenoses. That, in turn, lead to the development of low profile steerable catheters in the form of a balloon mounted directly to and carried by the steerable guidewire. Examples of such catheters are the USCI Probe catheter commercially available from USCI Division of C. R. Bard, Inc., Billerica, Mass. and the Hartzler LPS catheter commercially available from Advanced Cardiovascular Systems, Inc., Mountain View, Calif.

Although angioplasty catheters of the type having a balloon carried directly by the guidewire have met with acceptance, they are not free of difficulty. Among the problems presented by such catheters is that rotation of the steerable guidewire is hampered somewhat because the balloon tends to restrict rotation of the wire. Therefore, although the wire is steerable, it is not always steerable with the facility that may be desired. Another difficulty presented by such catheters is that the balloon or the tubular segment of the catheter proximal of the balloon and to which the balloon is attached may become somewhat bound, particularly when passed through tortuous coronary arteries. As a result, when the guidewire is rotated, the proximal tube and the balloon may become twisted thereby restricting or preventing flow of liquid inflation medium to or from the balloon.

It is among the general objects of the invention to provide an improved catheter incorporating an integral steerable guidewire and carrying a balloon which provides for a high degree of freedom of motion to facilitate manipulation of the guidewire.

It is also among the objects of the invention to provide a catheter having an integral steerable guidewire in which the balloon and the tubular segment to which it is mounted will not tend to adversely twist closed in response to rotation of the guidewire.

SUMMARY OF THE INVENTION

In one embodiment of the invention, the catheter includes an integral guidewire in the form of an elongate flexible metal shaft having tubular segments which define a lumen extending longitudinally along the shaft. A core wire is mounted to and extends from the distal end of the tubular segments. An elongate radiopaque spring like coil is mounted to the distal end of the core wire. The coil provides a relatively soft, atraumatic tip for the catheter as it is advanced through the patient's arteries. The spring tip may be bent to a curved configuration so that when the shaft is rotated, it can steer the bent distal end selectively to the intended branch of the patient's arteries. The radiopaque nature of the coil enables it to be visualized fluoroscopically.

A balloon is carried on the distal end of the shaft but in a manner such that its distal end is unattached to the shaft thereby enabling the guidewire to be rotated substantially independently of the balloon so that its rotation is not impaired. The proximal end of the balloon is attached to the end of an elongate outer sleeve, the proximal end of which is attached to the distal end of the tubular segment of the shaft. The distal end of the balloon is attached to the distal end of an inner sleeve, the proximal end of which is attached to and surrounds the core wire. The balloon may be inflated and deflated through the lumen in the shaft which communicates with the annular lumen defined between the outer and inner sleeves.

In a second embodiment of the invention, the balloon is mounted on the distal end of a plastic tube having two side-by side lumens. The two lumen tube is mounted at its proximal end at the juncture region of the tubular segment of the shaft and core wire. Two lumen tube includes an inflation lumen that communicates with the interior of the balloon and a core wire lumen through which the core wire extends. The two lumen tube is unattached to the shaft or core wire except at its proximal end. The distal end of the balloon is attached to the distal end of the core wire lumen and is attached at its proximal end to the dual lumen tube at a location that is proximal to the outlet for the inflation lumen.

It is among the general objects of the invention to provide an improved dilatation catheter having a balloon and an integral guidewire for PTCA in which the drag on the rotation of the guidewire is reduced.

A further object of the invention is to provide a PTCA balloon catheter having an integral guidewire in which the distal tip of the guidewire has increased responsiveness to rotation of the proximal shaft.

Another object of the invention is to provide a PTCA balloon catheter having an integral guidewire which provides the physician with better control over the manipulation of the integral guidewire.

Another object of the invention is to provide a PTCA balloon catheter having an integral guidewire which permits relatively unrestrained rotation of the guidewire and in a manner which does not tend to twist the inflation lumen or the balloon of the catheter closed or otherwise adversely restrict the flow area through the inflation lumen.

DESCRIPTION OF THE DRAWINGS

The foregoing and other objects and advantages of the invention will be appreciated more fully from the following further description with reference to the accompanying drawings in which.

DESCRIPTION OF THE ILLUSTRATIVE EMBODIMENTS

Figure 1:
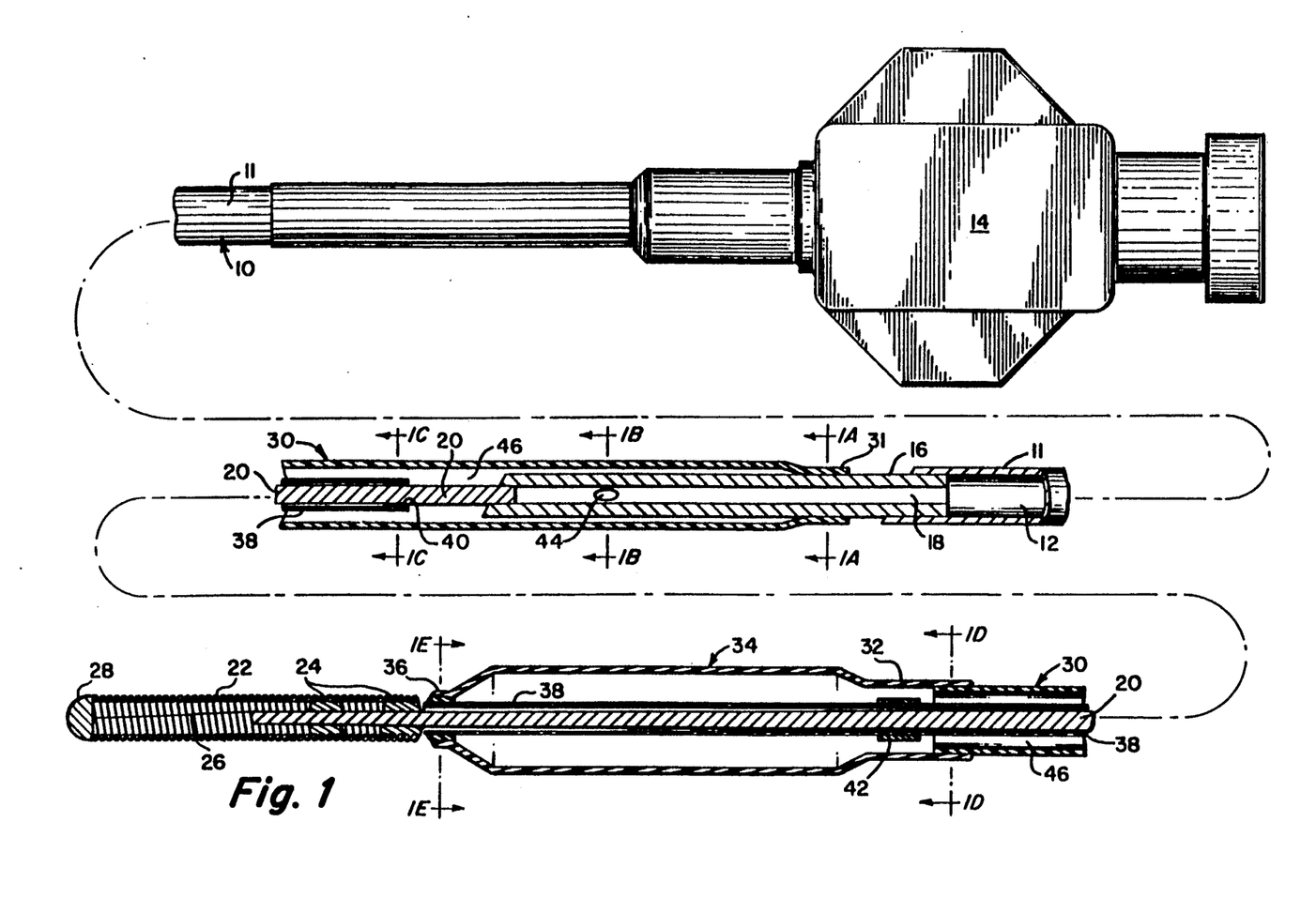
FIG. 1 is a fragmented sectional illustration of one embodiment of the catheter.
Figure 1A:
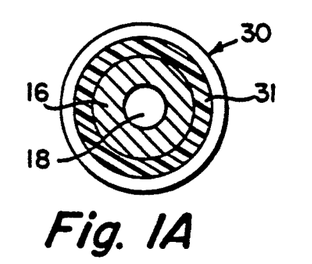
FIG. 1A is a cross-sectional illustration of the catheter as seen along the line 1A—1A of FIG. 1.
Figure 1B:
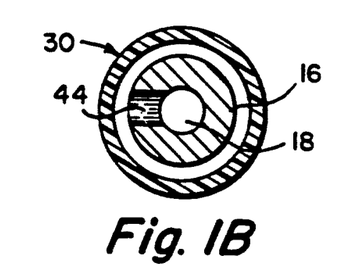
FIG. 1B is a cross sectional illustration of the catheter as seen along the line 1B—1B of FIG. 1.
Figure 1C:
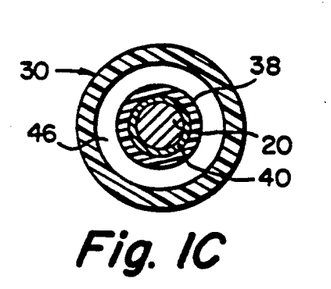
FIG. 1C is a cross sectional illustration of the catheter as seen along the line 1C—1C of FIG. 1.
Figure 1D:
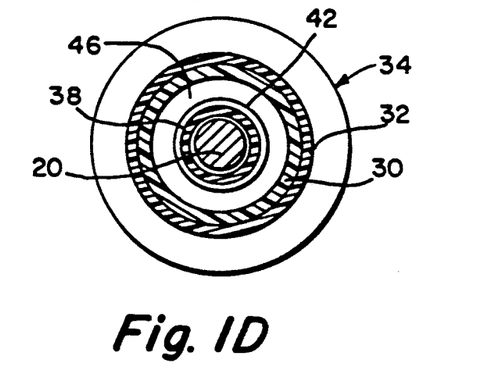
FIG. 1D is a cross-sectional illustration of the catheter as seen along the line 1D—1D of FIG. 1.
Figure 1E:
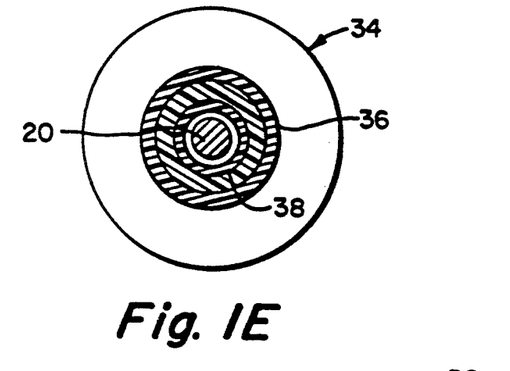
FIG. 1E is a cross sectional illustration of the catheter as seen along the line 1E—1E of FIG. 1.

FIG. 1 shows one embodiment of the invention in which the catheter includes an elongate flexible metal shaft indicated generally by the reference character 10 which may be formed from stainless steel hypodermic tubing. The overall length of the catheter may be of the order of 150 cm. The shaft 10 includes an elongate tubular proximal segment 11, about 100 cm long, an intermediate tubular segment 16, about 5 cm long, and a core wire 20 about 35 cm long. By way of example, the proximal segment of the shaft may be of the order of 0.022" diameter having a wall thickness of the order of 0.004" and may be coated with a thin film of high lubricity material, such as Teflon primer paint or the like. The tubular proximal and intermediate segments of the shaft 10 define lumens 12, 18 which communicate, as will be described, with the interior of the balloon 34 to inflate and deflate the balloon 34 on the distal end of the shaft. A fitting 14 is mounted on the proximal end of the shaft 10 to facilitate connection with an inflation device such as a syringe or other suitable device as will be appreciated by those skilled in the art. The shaft 10 has sufficient torsional rigidity so that it may transmit rotation effectively to the distal end of the catheter to control manipulation and steering of the distal end.

The short, tubular intermediate segment 16 is secured to the distal end of the proximal segment 11 of shaft 10 and has a lumen 18 which communicates with the lumen 12 of the proximal segment 11. The intermediate segment 16 forms a transition between the tubular segment 11 and the core wire 20 that extends to the distal tip of the catheter. The core wire 20 is formed from stainless steel wire and is attached, at its proximal end, to the distal end of the lumen 18 of the intermediate segment 16. The core wire 20 is tapered in a distal direction so that the device is of increasing flexibility toward the distal end. By way of example, the core wire 20 may be 35 cm long and may taper from a 0.008" diameter at its proximal end to a 0.002" diameter at its distal end.

A helical coil 22 is secured to the distal tip of the core wire 20 as by solder joints 24 with a portion of the helical coil extending distally beyond the distal tip of the core wire 20. The distal extension of the coil is highly flexible and presents an atraumatic tip to the interior of the patient's blood vessels. A stainless steel or tungsten or other material shaping ribbon 26 may be extended from the distal solder joint to a tip solder joint 28. The tip solder joint 28 is rounded to present a smooth surface. The coil may be of the order of 2 cm long and have an outer diameter of 0.014". It may be wound from 0.003" diameter wire, such as 92% platinum, 8% tungsten alloy wire.

In the embodiment shown in FIG. 1, the catheter includes an outer elongate sleeve 30 that is formed from an appropriate thin flexible plastic material such as medium to high density polyethylene. The outer sleeve 30 is adhesively attached at its proximal end 31 to the intermediate shaft 16 as by cyanoacrylate adhesive. The outer sleeve 30 may be of the order of 35 cm long and may have an outer diameter of about, 0.026" and a wall thickness of about 0.003". The distal end of the outer sleeve 30 is adhesively attached to the proximal neck 32 of the dilatation balloon 34.

The balloon 34 may be formed from polyethylene terephthalate in the manner described in U.S. Pat. No. 4,490,421 to Levy. By way of example, the balloon may be of the order of 1.5 to 2.5 cm long and may have a wall thickness of about 0.001" or less. The inflated diameter of the balloon 34 may be between about 1.5 to about 4.0 mm.

The distal end of the balloon 34 is attached, at its distal neck 36 to the distal end of an inner sleeve 38 that extends proximally about the tapered core wire 20 and is adhesively attached at its proximal end to the core wire by adhesive, as illustrated at 40. The inner sleeve is thin walled and may be formed from thermoset polyimide or other material such as thin walled polyethylene terephthalate, although the polyimide is preferred. The wall thickness of the inner sleeve preferably is of the order of 0.001" or less. The inner sleeve should have an inner diameter just slightly greater than the outer diameter of the core wire and may be of the order of 0.009" inner diameter. The outer diameter of the inner sleeve may be, for example, of the order of 0.0105" outer diameter. The inner sleeve 38 may be about 30 cm long. We have found that a polyimide sleeve commercially available from Polymicro Technology of Phoenix, Ariz. under the designation Micro Bore Polyimide #PPC229267 having the foregoing dimensions is satisfactory. The foregoing configuration results in an inner sleeve 38 which displays a substantial degree of column strength to resist axial buckling of the inner sleeve when it is subjected to an axial compressive load, such as when the catheter is advanced through a patient's blood vessel. The thin wall for the inner sleeve 38 permits a substantial amount of rotation to be absorbed by the inner sleeve, yet the inner sleeve will not buckle under axial loads because of the support of the core wire. It should be understood, however, that even though the inner diameter of the inner tube 38 is close to the outer diameter of the core wire the frictional characteristics of the two elements are such that they will not frictionally adversely impair rotation of the guidewire, particularly when the device is passed through the curves and tortuous anatomy of a patient's arteries. The polyimide material is sufficiently slippery as to avoid binding under such circumstances. Similarly, the frictional characteristics between the polyimide inner sleeve and the polyethylene outer sleeve are such that they do not restrict proper functioning of the device even when passed through tortuous bends of the arterial anatomy.

A radiopaque marker band 42 may be attached to the inner sleeve 38 in the region of the balloon to facilitate fluoroscopic determination of the position of the balloon in the patient's arteries.

The intermediate segment 16 is provided with one or more openings 44 to communicate the lumen 18 with the annular lumen 46 defined between the outer and inner sleeves 30, 38. Thus, it will be appreciated that the balloon 34 may be inflated and deflated by an inflation medium, such as a radiopaque contrast liquid through the lumens 12, 18, opening 44 and lumen 46.

From the foregoing, it will be appreciated that the balloon 34 and the outer and inner sleeves 30, 38 are unattached to the core wire except for the proximal connections 31, 40. Thus, when the catheter is disposed in the patient's artery and the shaft 10 is rotated from its proximal end, as would be done to manipulate and steer the distal end of the device, the rotation of the wire will not be appreciably restricted by the balloon or outer and inner sleeves 30, 38. Neither the balloon nor outer sleeve will become adversely twisted about the core wire 20. Instead, the rotational strain transmitted by the core wire or proximal portion 11 of the shaft 10 will be distributed along the length of the elongate inner and outer sleeves and is insufficient to cause appreciable adverse twisting of the balloon or outer sleeves. As a result, the inflation lumen remains open and the guidewire is provided with a high degree of rotational freedom even when the device is passed through highly tortuous anatomy. By way of example, the present invention enables the guidewire to be rotated at least five and as much as eight or more rotations with respect to the balloon without closing off the inflation lumen to the balloon. The catheter in accordance with the invention maintains an open inflation lumen even when the catheter is disposed in tortuous coronary anatomy.

Figure 3:
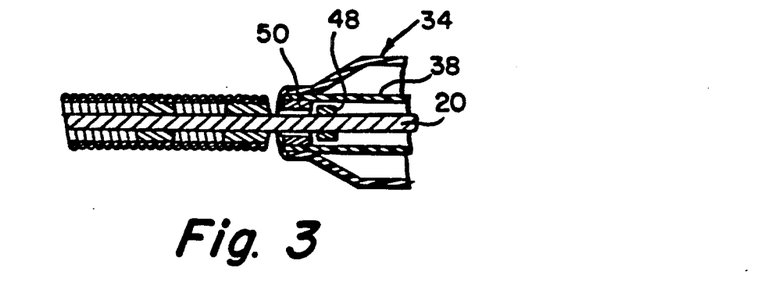
FIG. 3 is an illustration of the region of the distal end of the balloon incorporating a further modification to the invention by which the balloon and sleeves or two lumen tube are reinforced against longitudinal collapse.

As shown in FIG. 3, although the above-described cooperation of the thin wall inner sleeve 38 and core wire 20 provide adequate column strength, the catheter described above may be modified to include inner and outer thrusting rings 48, 50 adjacent the distal end of the balloon. The inner thrusting ring is mounted about the core wire 20 and is secured to the core wire. The outer thrusting ring 50 is annularly shaped and is adhesively attached to the distal end of the inner sleeve 38 with the core wire 20 protruding through a central hole in the outer ring. The inner ring 48 has a greater outer diameter than the central hole of the outer disk so that the inner and outer rings 48, 50 may abut each other to prevent the longitudinal collapse of the balloon and associated sleeves. Rings 48, 50 do not interfere with the free rotation of the core wire 20 with respect to the distal end of the balloon.

Figure 2:
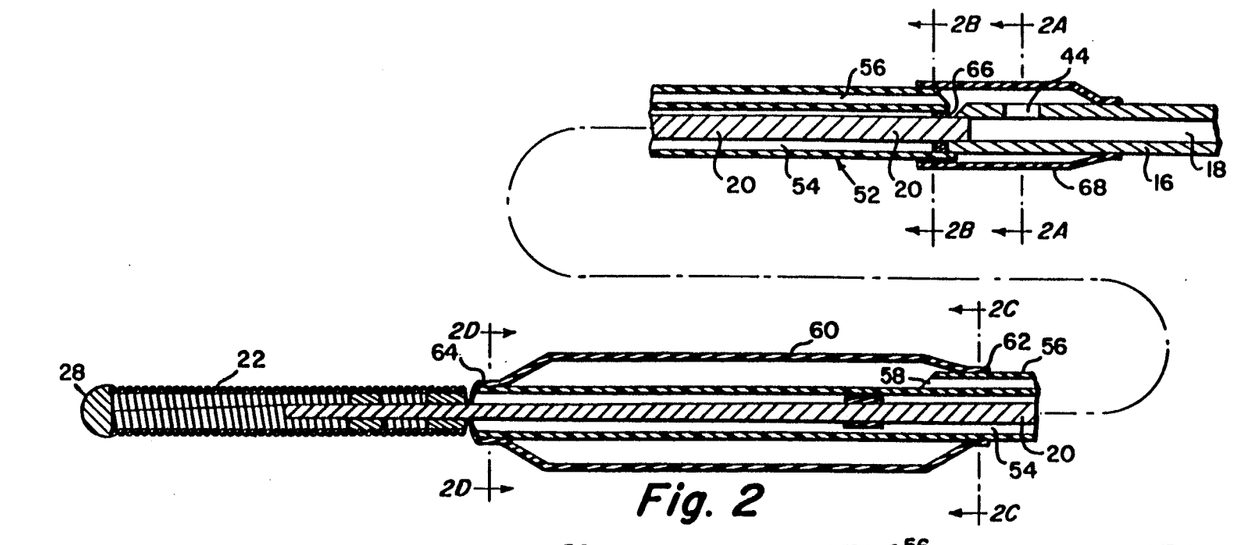
FIG. 2 is a fragmented cross-sectional illustration of another embodiment of the catheter.
Figure 2A:
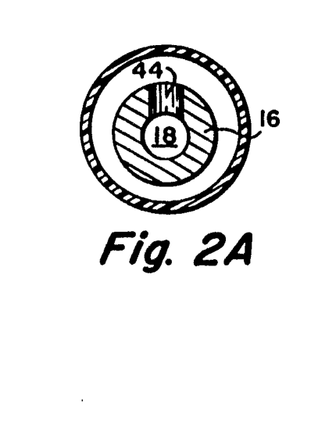
FIG. 2A is a cross sectional illustration of the catheter as seen along the line 2A—2A of FIG. 2.
Figures 2B, 2C:
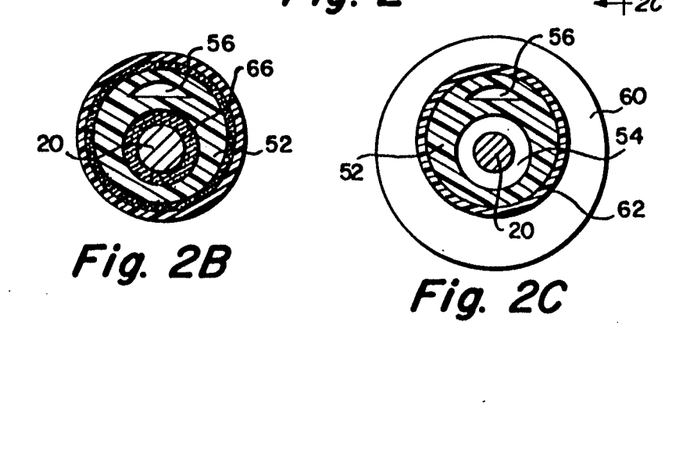
FIG. 2B is a cross sectional illustration of the catheter as seen along the line 2B—2B of FIG. 2.
FIG. 2C is a cross-sectional illustration of the catheter as seen along the line 2C—2C of FIG. 2.
Figure 2D:
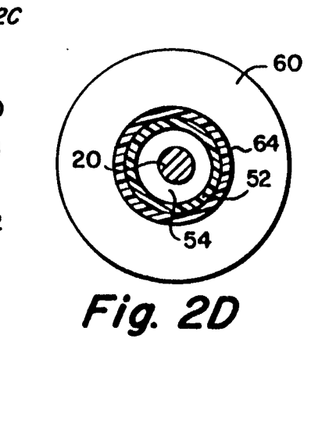
FIG. 2D is a cross-sectional illustration of the catheter as seen along the line 2D—2D of FIG. 2.

FIG. 2 illustrates another embodiment of the invention. In this embodiment, a two lumen tube 52 is provided in place of the concentric sleeves. The tube 52 is flexible and may be formed of an appropriate plastic such as low to medium density polyethylene. The tube may have an outer diameter of about 0.024". The tube 52 may be of the order of 30-35 cm long. The tube may be formed by extrusion and defines a core wire lumen 54 which receives the core wire and an inflation lumen 56.

The inflation lumen 56 terminates short of the distal end of the tube 52 in a port 58 which opens into the interior of the balloon 60. The balloon 60 is adhesively attached at its proximal end to the two lumen portion of the tube 52, as indicated at 62. The distal end of the balloon is attached, at 64, to the distal end of the tube 52 which defines the core wire lumen 54. The tube 52 is attached to the proximal end of the core wire by adhesive, as indicated at 66 which constitutes the sole point of attachment of the tube 52 to the guidewire. A plastic tubular connector sleeve 68 encloses the juncture of the tube 52 with the core wire 20 and extension tube 16. The sleeve 68 is attached adhesively at its proximal end to the intermediate portion 16 proximally of the outlet 44 and at its distal end, to the proximal end of the two lumen tube. The sleeve serves to confine and communicate the lumen 18 of the intermediate shaft 16 with the inflation lumen 56 of the tube 52, through opening 44.

The embodiment in FIG. 2 is in all other respects the same as that described in connection with the embodiment of FIG. 1. It should be noted that the embodiment in FIG. 2 also may be provided with thrusting rings 48, 50 as described above in connection with the embodiment of FIG. 1.

From the foregoing, it will be appreciated that the invention provides a balloon dilatation catheter having an integral guidewire in which the balloon will not impair the ability to manipulate the guidewire. Additionally, the invention provides for a catheter of the type described having reduced tendency for the balloon to become adversely twisted about the wire. Rotation of the guidewire will not cause the inflation lumen to become adversely restricted or closed off.

Although the invention has been described with particular reference to a balloon dilatation catheter usable in percutaneous transluminal coronary angioplasty (PTCA), the invention is equally usable for balloon dilatation catheters used in other vessels, such as peripheral blood vessels.

It should be understood that the foregoing description of the invention is intended merely to be illustrative thereof and that other modifications and embodiments may be apparent to those skilled in the art without departing from its spirit.

Having thus described the invention what I desire to claim and secure by letters patent is:

1. A balloon dilation catheter comprising:
   an elongate shaft having proximal and distal ends;
   an elongate tubular means defining two lumens, the tubular means being attached to the shaft only at the proximal end of the tubular means, a portion of the shaft extending through one of the lumens in the tubular means, whereby limited rotational movement between the tubular means and the shaft may occur;
   a balloon carried by the tubular means, the balloon and the distal end of the tubular means being unattached to the shaft;
   the other of the lumens being in communication with the interior of the balloon;
   the shaft having inflation lumen means communicating with the inflation lumen in the tubular means for inflating and deflating the balloon.

2. A balloon dilation catheter as defined in claim 1 wherein the shaft is sufficiently torsionally rigid so that it may transmit rotation controllably from the proximal end of the shaft to the distal end of the shaft.

3. A catheter as defined in claims 1 or 2 wherein the shaft comprises:
an elongate flexible shaft tube, and a core wire connected to and extending distally from the shaft tube.

4. A catheter as defined in claim 3 wherein said tubular means comprises:
an outer flexible plastic sleeve mounted on the distal portion of the shaft having a proximal end attached to the shaft tube;
an inner sleeve disposed within the outer sleeve and enclosing a portion of the core wire, the proximal end of the inner sleeve being attached to the shaft in the region of the proximal portion of the core wire, said inner and outer sleeves being unattached to the shaft except at their proximal ends;
the balloon being mounted to the distal ends of the inner and outer sleeves.

5. A catheter as defined in claim 3 wherein the tubular means comprises:
an elongate flexible plastic tubular member having an inflation lumen and a core wire lumen extending therethrough, the core wire lumen receiving the core wire, the plastic tubular member being attached, at its proximal end, to the shaft in the region of the proximal end of the core wire;
the inflation lumen of the tubular plastic member being shorter than the core wire lumen and extending from the proximal end of the tubular plastic member to a location proximal of the distal end of the core wire lumen;
the balloon being mounted at its proximal end to the plastic tubular member at a location proximal of the outlet of the inflation lumen, the distal end of the balloon being mounted to the distal end of the plastic tubular member about the core wire lumen; and
the inflation lumen in the shaft being in communication with the inflation lumen in the tubular plastic member.

6. A catheter as defined in claim 5 wherein the tubular member is attached to the proximal end of the core wire by adhesive.

7. A catheter as defined in claim 5 wherein the means communicating the shaft lumen with the inflation lumen in the plastic member comprises an opening formed through the wall of the shaft tube and a sleeve enclosing the distal end of the shaft tube and the proximal end of the two lumen plastic tubular member for confining fluid flow between the opening and the inflation lumen of the plastic tubular member.

8. A catheter as defined in claim 3 further comprising an elongate flexible helical coil mounted to the distal end of the shaft and extending distally of the balloon.

9. A catheter as defined in claim 1 further comprising an elongate flexible helical coil mounted to the distal end of the shaft and extending distally of the balloon.

10. A catheter as defined in claim 4 further comprising an elongate flexible helical coil mounted to the distal end of the shaft and extending distally of the balloon.

11. A catheter as defined in claim 5 further comprising an elongate flexible helical coil mounted to the distal end of the shaft and extending distally of the balloon.

12. A catheter as defined in claim 1 further comprising:
thrust means for resisting longitudinal collapse of the balloon and the elongate tubular means in a proximal direction.

13. A catheter as defined in claim 3 further comprising:
thrust means for resisting longitudinal collapse of the balloon and the elongate tubular means in a proximal direction.

14. A catheter as defined in claim 4 further comprising:
thrust means for resisting longitudinal collapse of the balloon and the elongate tubular means in a proximal direction.

15. A catheter as defined in claim 12 wherein the thrust means comprises a first distal thrust ring mounted to the distal end of the elongate tubular member, the ring having a central aperture through which the shaft passes and
a proximal thrust ring mounted to the shaft proximally of the distal thrust ring for abutment by the distal thrust ring.

16. A catheter as defined in claim 5 further comprising:
thrust means for resisting longitudinal collapse of the balloon and the elongate tubular means in a proximal direction.

17. A catheter as defined in claim 13 wherein the thrusting means comprises:
a distal thrust ring mounted to the distal end of the elongate tubular member, the ring having a central aperture through which the shaft passes; and
a proximal thrusting ring mounted to the shaft proximally of the distal thrusting ring for abutment by the distal thrusting ring.

18. A catheter as defined in claim 14 wherein the thrust means comprises:
a distal thrust ring mounted to the distal end of the elongate tubular member, the ring having a central aperture through which the shaft passes; and
a proximal thrust ring mounted to the shaft proximally of the distal thrust ring for abutment by the distal thrust ring.

19. A catheter as defined in claim 15 wherein the thrust means comprises:
a distal thrust ring mounted to the distal end of the elongate tubular member, the ring having a central aperture through which the shaft passes; and
a proximal thrust ring mounted to the shaft proximally of the distal thrust ring for abutment by the distal thrust ring.

20. A catheter as defined in claim 1 dimensioned to be percutaneously insertable into a patient's artery and advanceable into the patient's coronary arteries.

21. A catheter as defined in claim 3 dimensioned to be percutaneously insertable into a patient's artery and advanceable into the patient's coronary arteries.

22. A catheter as defined in claim 4 dimensioned to be percutaneously insertable into a patient's artery and advanceable into the patient's coronary arteries.

23. A catheter as defined in claim 5 dimensioned to be percutaneously insertable into a patient's artery and advanceable into the patient's coronary arteries.

24. A catheter as defined in claim 6 dimensioned to be percutaneously insertable into a patient's artery and advanceable into the patient's coronary arteries.

25. A catheter as defined in claim 7 dimensioned to be percutaneously insertable into a patient's artery and advanceable into the patient's coronary arteries.

26. A catheter as defined in claim 8 dimensioned to be percutaneously insertable into a patient's artery and advanceable into the patient's coronary arteries.

27. A catheter as defined in claim 12 dimensioned to be percutaneously insertable into a patient's artery and advanceable into the patient's coronary arteries.

28. A catheter as defined in claim 13 dimensioned to be percutaneously insertable into a patient's artery and advanceable into the patient's coronary arteries.

29. A catheter as defined in claim 14 dimensioned to be percutaneously insertable into a patient's artery and advanceable into the patient's coronary arteries.

30. A catheter as defined in claim 15 dimensioned to be percutaneously insertable into a patient's artery and advanceable into the patient's coronary arteries.

31. A catheter as defined in claim 16 dimensioned to be percutaneously insertable into a patient's artery and advanceable into the patient's coronary arteries.

32. A catheter as defined in claim 17 dimensioned to be percutaneously insertable into a patient's artery and advanceable into the patient's coronary arteries.

33. A catheter as defined in claim 18 dimensioned to be percutaneously insertable into a patient's artery and advanceable into the patient's coronary arteries.

34. A catheter as defined in claim 19 dimensioned to be percutaneously insertable into a patient's artery and advanceable into the patient's coronary arteries.

35. A balloon dilatation catheter as defined in claim 1 wherein said limited rotational movement includes at least five rotations of the shaft with respect to the balloon.

36. A balloon dilation catheter as defined in claim 4 wherein said limited rotational movement includes at least five rotations of the elongate shaft with respect to the balloon.

37. A catheter as defined in claim 5 wherein the limited rotational movement includes at least five rotations of the shaft with respect to the balloon.

38. A catheter as defined in claim 4 further comprising:
the inner sleeve having a thin wall and having an inner diameter slightly greater than the outer diameter of the core wire whereby the thin walled inner sleeve may be supported against longitudinal buckling.

39. A catheter as defined in claim 4 further comprising:
the inner and outer sleeves and the core wire being formed from materials having relatively low coefficients of friction with respect to each other.

40. A catheter as defined in claim 39 wherein the outer sleeve is formed from polyethylene and the inner sleeve is formed from polyimide.

41. A catheter as defined in claims 1 or 2 wherein the shaft is formed from metal.

42. A catheter as defined in claim 3 wherein the shaft is formed from metal.

43. A catheter as defined in claim 4 wherein the shaft is formed from metal.

44. A catheter as defined in claim 5 wherein the shaft is formed from metal.

45. A catheter as defined in claim 3 wherein the shaft further comprises:
a proximal tubular segment and an intermediate, relatively short tube mounted to the distal end of the proximal segment and having an outer diameter smaller than that of the proximal segment;
the core wire being attached to the distal end of the intermediate segment and extending distally therefrom.

46. A catheter as defined in claim 45 wherein said tubular means comprises:
an outer flexible plastic sleeve mounted on the distal portion of the shaft having a proximal end attached to the intermediate segment of the shaft;
an inner sleeve disposed within the outer sleeve and enclosing a portion of the core wire, the proximal end of the inner sleeve being attached to the proximal portion of the core wire, said inner and outer sleeves being unattached to the shaft except at their proximal ends;
the balloon being mounted to the distal ends of the inner and outer sleeves.

47. A catheter as defined in claim 45 wherein the tubular means comprises:
an elongate flexible plastic tubular member having two lumens extending therethrough, one of the lumens receiving the core wire, the tubular member being attached, at its proximal end, to the proximal end of the core wire;
the other lumen of the tubular plastic member being shorter and extending from the proximal end of the tubular plastic member to a location proximal of the distal end of the first lumen;
the balloon being mounted at its proximal end to the plastic tubular member at a location proximal of the outlet of the inflation lumen, the distal end of the balloon being mounted to the distal end of the plastic tubular member about the first lumen; and
means communicating the lumen in the intermediate shaft segment with the proximal end of the inflation lumen in the tubular plastic member.

48. A catheter as defined in claims 1 or 2 wherein the portion of the shaft that extends through one of the lumens comprises a core wire of increasing flexibility in a distal direction.

49. A catheter as defined in claim 3 wherein the distal portion of the core wire is of increasing flexibility in a distal direction.

50. A catheter as defined in claim 4 wherein a distal portion of the core wire is of increasing flexibility in a distal direction.

51. A catheter as defined in claim 5 wherein the core wire within the core wire lumen is of increasing flexibility in a distal direction.

52. A catheter as defined in claim 8 wherein the distal portion of the core wire is of increasing flexibility in a distal direction.

53. A catheter as defined in claim 48 wherein the core wire is tapered.

54. A catheter as defined in claim 49 wherein the core wire is tapered.

55. A catheter as defined in claim 50 wherein the core wire is tapered.

56. A catheter as defined in claim 51 wherein the core wire is tapered.

57. A catheter as defined in claim 52 wherein the core wire is tapered.

58. A catheter as defined in claim 4 wherein the inner sleeve is attached to the core wire by adhesive.

59. In a balloon dilation catheter having proximal and distal ends, an elongate flexible shaft having a balloon mounted on its distal end and an inflation lumen extending lengthwise of the shaft in communication with the interior of the balloon and a fitting on the proximal end of the shaft for communication with the inflation lumen, an improved construction for the distal end of the catheter comprising:

elongate flexible tubular means having a first lumen which is a continuation of the inflation lumen in the shaft, and a second lumen defining a core wire lumen;

the balloon being located on the tubular means and being in communication with the first lumen;

an elongate core wire extending distally through the second lumen of the elongate tubular means;

that portion of the elongate tubular means that defines the second lumen being connected to the core wire at a proximal connection located substantially proximally of the distal end of the core wire lumen, the elongate tubular means being unattached to the core wire distally of the proximal connection thereby to enable limited rotational movement of the core wire within the second lumen and with respect to the elongate tubular means;

said catheter including means for transmitting rotation to the core wire from the proximal end of the catheter to cause rotation of the core wire with respect to the elongate tubular means.

60. An improved construction for the distal end of a catheter as defined in claim 59 wherein the elongate tubular means comprises:

an outer flexible plastic sleeve;

an inner plastic sleeve disposed within the outer sleeve and defining the second lumen, an annular region between the inner and outer sleeves defining the first lumen;

the proximal end of the inner sleeve being connected to the core wire at said proximal connection;

the proximal end of the balloon being carried by the distal end of the outer sleeve;

the distal end of the balloon being carried by the distal end of the inner sleeve.

61. An improved construction for the distal end of a balloon dilation catheter as defined in claim 59 wherein the tubular means comprises:

an elongate flexible plastic tubular member having said first and second lumens formed therein;

the proximal end of the elongate flexible plastic tubular member being attached to the core wire at said proximal connection;

the second lumen being longer than the first lumen;

the balloon being mounted at its proximal end to the plastic tubular member at a location proximal of the inflation lumen outlet, the distal end of the balloon being mounted to the distal end of the plastic tubular member.

62. An improved construction for the distal end of a balloon dilation catheter as defined in any one of claims 59–61 wherein the means for transmitting rotation from the proximal end to the distal end of the catheter comprises the catheter shaft being formed from a torsionally rigid material.

63. An improved construction for the distal end of a balloon dilation catheter as defined in claim 62 wherein the shaft is formed from metal tubing defining said inflation lumen and the core wire is connected to the distal end of the metal tubing.

64. An improved construction for the distal end of a balloon dilation catheter as defined in any one of claims 59–61 further comprising an elongate flexible helical coil mounted to the distal end of the core wire and extending distally of the balloon.

65. An improved construction for the distal end of a balloon dilation catheter as defined in any one of claims 59–61 wherein said limited rotational movement includes at least five rotations of the core wire with respect to the balloon.

66. An improved construction for the distal end of a balloon dilation catheter as defined in any one of claims 59–61 wherein the distance from the proximal connection to the end of the core wire is about 35 cm.

67. An improved construction for the distal end of a balloon dilation catheter as defined in claim 62 wherein the distance from the proximal connection to the end of the core wire is about 35 cm.

68. An improved construction for the distal end of a balloon dilation catheter as defined in any one of claims 59–61 wherein the second lumen is about 30 cm long.

69. An improved construction for the distal end of a balloon dilation catheter as defined in claim 62 wherein the second lumen is about 30 cm long.

70. In a balloon dilation catheter having proximal and distal ends, an elongate flexible shaft having a balloon mounted on its distal end and an inflation lumen extending lengthwise of the shaft in communication with the interior of the balloon and a fitting on the proximal end of the shaft for communication with the inflation lumen, an improved construction for the distal end of the catheter comprising:

elongate flexible tubular means having a first lumen which is a continuation of the inflation lumen in the shaft, and a second lumen defining a core wire lumen;

the balloon being located on the tubular means and being in communication with the first lumen;

an elongate core wire extending distally through the second lumen of the elongate tubular means;

that portion of the elongate tubular means that defines the second lumen being connected to the core wire at a proximal connection located substantially proximally of the distal end of the core wire lumen, the elongate tubular means being unattached to the core wire distally of the proximal connection thereby to enable limited rotational movement of the core wire within the second lumen and with respect to the elongate tubular means;

said catheter including means for transmitting rotation to the core wire from the proximal end of the catheter to cause rotation of the core wire with respect to the elongate tubular means;

an elongate tubular element extending through the balloon and connected at its distal end to the distal end of the balloon, the tubular element containing at least a portion of the core wire and being connected to the core wire at said location proximally of the balloon, said tubular element being constructed and arranged to twist and absorb relative rotation between the core wire and the balloon;

said elongate tubular element also having a means communicating the inflation lumen with the interior of the balloon.

71. In a balloon dilation catheter having proximal and distal ends, an elongate flexible shaft having a balloon mounted on its distal end and an inflation lumen extending lengthwise of the shaft in communication with the interior of the balloon and a fitting on the proximal end of the shaft for communication with the inflation lumen, an improved construction for the distal end of the catheter comprising:

elongate flexible tubular means having a first lumen which is a continuation of the inflation lumen in the shaft, and a second lumen defining a core wire lumen;

the balloon being located on the tubular means and being in communication with the first lumen;

an elongate core wire extending distally through the second lumen of the elongate tubular means;

that portion of the elongate tubular means that defines the second lumen being connected to the core wire at a proximal connection located substantially proximally of the distal end of the core wire lumen, the elongate tubular means being unattached to the core wire distally of the proximal connection thereby to enable limited rotational movement of the core wire within the second lumen and with respect to the elongate tubular means;

said catheter including means for transmitting rotation to the core wire from the proximal end of the catheter to cause rotation of the core wire with respect to the elongate tubular means;

an elongate tubular element extending through the balloon and connected at its distal end to the distal end of the balloon, the tubular element containing at least a portion of the core wire and being connected to the core wire at said location proximally of the balloon, said tubular element being constructed and arranged to twist and absorb relative rotation between the core wire and the balloon;

said tubular element comprising inner and outer sleeves, the inner sleeve receiving the core wire, the annular space between the inner and outer sleeves defining means communicating the inflation lumen with the interior of the balloon.

* * * * *